United States Patent [19]

Billington et al.

[11] Patent Number: 5,254,561
[45] Date of Patent: Oct. 19, 1993

[54] TRICYCLIC ANTIPSYCHOTIC AGENTS

[75] Inventors: David C. Billington, Lavallois Perret, France; Michael G. N. Russell, Welwyn Garden City, England

[73] Assignee: Merck Sharp & Dohme Limited, Hoddesdon, England

[21] Appl. No.: 716,880

[22] Filed: Jun. 18, 1991

[30] Foreign Application Priority Data

Jun. 25, 1990 [GB] United Kingdom ............. 9014061

[51] Int. Cl.$^5$ ............. A61K 31/435; C07D 221/06; C07D 491/056
[52] U.S. Cl. ........................... 514/290; 514/287; 546/65; 546/93; 546/111
[58] Field of Search ............. 546/93, 111, 65; 514/287, 290

[56] References Cited

U.S. PATENT DOCUMENTS 4,740,602 4/1988 Böttcher et al. ............. 548/406

FOREIGN PATENT DOCUMENTS

| 20005441 | 6/1990 | Canada. |
| 206225 | 9/1987 | European Pat. Off.. |
| 0410535 | 1/1991 | European Pat. Off.. |
| WO90/06927 | 6/1990 | PCT Int'l Appl.. |

OTHER PUBLICATIONS

J. Med. Chem., 1974, 17, 1040.
J. Med. Chem., 1978, 21, 340.
Julien, et al., Eur. J. Pharmacol., 1990. 183, 2145.
Pascaud, et al., J. Pharmacol. Exp. Ther., 1990, 255, 1354.

Primary Examiner—C. Warren Ivy
Assistant Examiner—James H. Turnipseed
Attorney, Agent, or Firm—Robert J. North; William Nicholson; Joseph F. DiPrima

[57] ABSTRACT

A class of 2,3,4,4a,9,9a-hexahydro-1H-indeno[2,1-c]pyridine and 2,3,4,4a,5,6,7,11b-octahydro-1H-benzo[3,4]cyclohepta[1,2-c]pyridine derivatives are selective ligands at sigma recognition sites and are therefore useful in the treatment and/or prevention of psychiatric and/or gastrointestinal disorders.

6 Claims, No Drawings

TRICYCLIC ANTIPSYCHOTIC AGENTS

This invention relates to a class of fused tricyclic compounds. More particularly, the invention relates to hexahydro-1H-indeno[2,1-c]pyridine and octahydro-1H-benzo[3,4]cyclohepta[1,2-c]pyridine derivatives which are selective ligands at sigma recognition sites and are therefore useful in the treatment of psychiatric and/or gastrointestinal disorders.

Certain hexahydro-1H-indeno[2,1-c]pyridine derivatives are known. For example, *J. Med. Chem.*, 1974, 17, 1040 describes the preparation of N-methyl2,3,4,4a,9-,9a-hexahydro-1H-indeno[2,1-c]pyridine as a probe for analgesic activity. A class of 9-phenylsubstituted 2,3,4,4a,9,9a-hexahydro-1H-indeno[2,1-c]pyridine derivatives is described in *J. Med. Chem.*, 1978, 21, 340; these compounds are reported to be active in a range of assays against induced ventricular arrhythmias. In neither of the aforementioned documents, however, is there any disclosure or suggestion that the compounds disclosed therein might manifest beneficial interactions with sigma recognition sites.

U.S. Pat. No. 4,740,602 describes a class of compounds containing an indol-3-yl ring system and inter alia a 1,2,3,4-tetrahydro-2-azafluorene or 1,2,3,4,6,7-hexahydro-3-aza-5H-dibenzo[a,c]cycloheptene ring system, the two ring systems being separated by a $C_{2-5}$ alkylene chain or a bridging chain of formula $—CH_2—S(O)_x—CH_2CH_2—$, in which x is zero, 1 or 2. These compounds are stated to exhibit inter alia neuroleptic properties. However, analgesic and hypotensive side-effects are also mentioned for these compounds, detracting from any specificity they might possess as neuroleptics.

Published European Patent Application No. 0410535 describes a class of octahydrobenz[f]isoquinoline derivatives which have interesting activity as selective ligands at sigma recognition sites and which are therefore of value as neuroleptic agents.

Most of the numerous currently available clinically effective antipsychotic drugs are dopamine $D_2$ receptor antagonists. As a result, they produce a characteristic spectrum of undesirable side-effects. These include endocrine effects and extrapyramidal side-effects, as well as often irreversible tardive dyskinesia. In addition, $D_2$ receptor antagonists are only palliative. They tend to alleviate only certain schizophrenic behaviour, especially the "positive" symptoms of florid delusions and hallucinations, with much less effect on the "negative" symptoms of emotional withdrawal.

From receptor binding studies, it has been shown that many effective neuroleptic agents are ligands at sigma recognition sites in the brain. Various compounds are known which are capable of interacting with the sigma recognition site, and it is considered that this interaction is significant in the manifestation of their neuroleptic properties. Most of these compounds, however, also display significant activity at the dopamine $D_2$ receptor and consequently elicit the undesirable side-effects referred to above. For example, haloperidol, a widely used neuroleptic agent, interacts equally potently with sigma sites and $D_2$ receptors.

One compound which is essentially inactive at dopamine $D_2$ receptors is rimcazole. However, whilst showing some antischizophrenic activity, rimcazole displays only moderate potency at sigma sites.

The analgesic compound N-allylnormetazocine (SKF 10047), whilst having an affinity for the sigma recognition site, also interacts strongly with the N-methyl-D-aspartate (NMDA) ion-channel complex, and thereby evokes a variety of psychotic symptoms including disorientation, excitement and hallucinations.

Recently, it has been reported that sigma ligands dose-dependently stimulate duodenal bicarbonate secretion in rats (see, for example, Julien et al., *Eur. J. Pharmacol.*, 1990, 183, 2145; and Pascaud et al., *J. Pharmacol. Exp. Ther.*, 1990, 255, 1354). Sigma site ligands are thus of potential utility in the control of gastrointestinal disorders.

We have now found a class of potent, selective ligands at sigma recognition sites displaying negligible activity at $D_2$, NMDA and other CNS receptors, which are therefore of value in the treatment of psychiatric and/or gastrointestinal disorders.

The present invention accordingly provides the use of a compound of formula I or a pharmaceutically acceptable salt thereof:

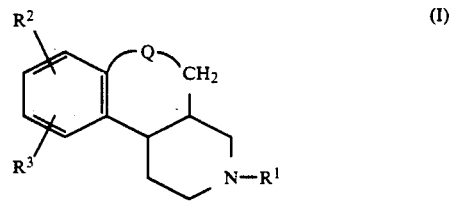

wherein

Q represents a bond or a group of formula $—(CH_2)_2—$;

$R^1$ represents hydrocarbon;

$R^2$ and $R^3$ independently represent hydrogen, hydrocarbon, halogen, cyano, trifluoromethyl, nitro, $—OR^x$, $—SR^x$, $—NR^xR^y$, $—CO_2R^x$ or $—CONR^xR^y$, or together represent methylenedioxy; and $R^x$ and $R^y$ independently represent hydrogen or hydrocarbon;

for the manufacture of a medicament for the treatment and/or prevention of psychiatric disorders.

The present invention further provides the use of a compound of formula I as defined above or a pharmaceutically acceptable salt thereof for the manufacture of a medicament for the treatment and/or prevention of gastrointestinal disorders.

The term "hydrocarbon" as used herein includes straight-chained, branched and cyclic groups, including heterocyclic groups, containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-10}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl and heteroaryl($C_{1-6}$)alkyl.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are n-propyl, iso-propyl, n-butyl and t-butyl.

Suitable alkenyl groups include straight-chained and branched alkenyl groups containing from 2 to 6 carbon atoms. Typical examples include vinyl, allyl, butenyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 10 carbon atoms. Particular cycloalkyl groups are cyclopropyl, cyclohexyl and adamantyl.

Suitable aryl groups include phenyl and naphthyl groups.

Particular aryl($C_{1-6}$)alkyl groups are benzyl and phenethyl.

Suitable heterocycloalkyl groups include pyrrolidinyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, thienyl, benzthienyl, imidazolyl, oxadiazolyl and thiadiazolyl groups. Particular heteroaryl groups are pyridyl and furyl.

The hydrocarbon group may in turn be optionally substituted by one or more groups selected from $C_{1-6}$ alkyl, adamantyl, phenyl, halogen, $C_{1-6}$ haloalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, optionally substituted arylcarbonyloxy, $C_{2-6}$ alkylcarbonyl, optionally substituted arylcarbonyl, $C_{1-6}$ alkylthio, $C_{1-6}$ alkylsulphinyl, $C_{1-6}$ alkylsulphonyl, amino, mono- or di($C_{1-6}$)alkylamino, $C_{2-6}$ alkylcarbonylamino and $C_{2-6}$ alkoxycarbonylamino.

The term "halogen" as used herein includes fluorine, chlorine, bromine and iodine, especially chlorine.

Certain compounds falling within the definition of formula I above are novel. Accordingly, in a further aspect the present invention provides a compound of formula II or a salt thereof:

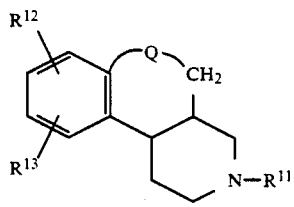

(II)

wherein

Q represents a bond or a group of formula —($CH_2$)$_2$—;

$R^{11}$ represents hydrocarbon;

$R^{12}$ and $R^{13}$ independently represent hydrogen, hydrocarbon, halogen, cyano, trifluoromethyl, nitro, —$OR^x$, —$SR^x$, —$NR^xR^y$, —$CO_2R^x$ or —$CONR^xR^y$, or together represent methylenedioxy; and $R^x$ and $R^y$ independently represent hydrogen or hydrocarbon;

provided that, when Q represents a bond and $R^{12}$ and $R^{13}$ each represents hydrogen, then $R^{11}$ does not represent methyl.

In a still further aspect, the present invention provides a pharmaceutical composition comprising a compound of formula II as defined above or a pharmaceutically acceptable salt thereof in association with one or more pharmaceutically acceptable carriers and/or excipients.

The invention also provides a compound of formula II as defined above or a pharmaceutically acceptable salt thereof for use in therapy.

For use in medicine, the salts of the compounds of formula II will be non-toxic pharmaceutically acceptable salts. Other salts may, however, be useful in the preparation of the compounds according to the invention or of their non-toxic pharmaceutically acceptable salts.

Suitable pharmaceutically acceptable salts of the compounds of formulae I and II above include acid addition salts which may, for example, be formed by mixing a solution of the compound according to the invention with a solution of a pharmaceutically acceptable non-toxic acid such as hydrochloric acid, fumaric acid, maleic acid, succinic acid, acetic acid, citric acid, tartaric acid, carbonic acid or phosphoric acid.

Suitable values for the substituent $R^{11}$ in the compounds of formula II above include optionally substituted $C_{3-6}$ alkyl, for example n-propyl or n-butyl; optionally substituted $C_{3-10}$ cycloalkyl, for example cyclohexyl or adamantyl; optionally substituted $C_{3-7}$ cycloalkyl($C_{1-6}$)alkyl, for example cyclohexylmethyl; optionally substituted aryl($C_{1-6}$)alkyl, for example benzyl, methylbenzyl, methoxybenzyl or phenethyl; and optionally substituted heteroaryl($C_{1-6}$)alkyl, for example furylmethyl or picolyl.

Examples of the substituents $R^{12}$ and $R^{13}$ in the compounds of formula II above include hydrogen, chlorine, $C_{1-6}$ alkyl and $C_{1-6}$ alkoxy. Suitably one of $R^{12}$ and $R^{13}$ represents hydrogen and the other represents hydrogen, chlorine, methyl or methoxy, especially hydrogen or methoxy. Preferably, $R^{12}$ and $R^{13}$ both represent hydrogen. When $R^{12}$ and $R^{13}$ in the compounds of formula II above are other than hydrogen, they may be present at any desired position of the aromatic moiety.

The compounds of formulae I and II above have at least two asymmetric centres, and may accordingly exist both as enantiomers and as diastereoisomers. In particular, the ring junction of the piperidino moiety with the rest of the ring system may be cis or trans. It is to be understood that all such isomers and mixtures thereof are encompassed within the scope of the present invention.

Preferred compounds of formula II above are those wherein the ring junction is trans.

One sub-class of compounds according to the invention is represented by the compounds of formula IIA and salts thereof:

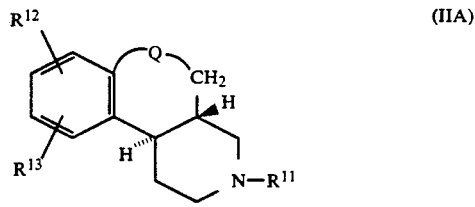

(IIA)

wherein Q, $R^{11}$, $R^{12}$ and $R^{13}$ are as defined above with reference to formula II; in particular wherein $R^{11}$ represents $C_{3-6}$ alkyl, $C_{2-6}$ alkenyl, $C_{3-10}$ cycloalkyl, $C_{3-7}$ cycloalkyl($C_{1-6}$)alkyl, aryl($C_{1-6}$)alkyl or heteroaryl($C_{1-6}$)alkyl, any of which groups may be optionally substituted. Preferred values of $R^{11}$ in the compounds of formula IIA are n-propyl, n-butyl, butenyl, dimethylallyl, cyclohexyl, adamantyl, cyclopropylmethyl, benzyl, methoxybenzyl and phenethyl.

A further sub-class of compounds according to the invention is represented by the compounds of formula IIB and salts thereof:

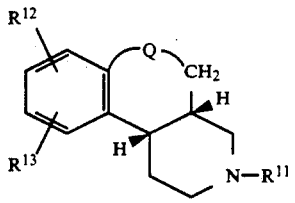
(IIB)

wherein Q, $R^{11}$, $R^{12}$ and $R^{13}$ are as defined above with reference to formula II; in particular wherein $R^{11}$ represents $C_{3-6}$ alkyl or $C_{3-10}$ cycloalkyl, especially n-butyl or cyclohexyl.

Specific compounds within the scope of the present invention include:

2-butyl-2,3,4,4a,9,9a-hexahydro-1H-indeno[2,1-c]pyridine;

3-butyl-2,3,4,4a,5,6,7,11b-octahydro-1H-benzo[3,4]cyclohepta[1,2-c]pyridine;

3-cyclohexyl-2,3,4,4a,5,6,7,11b-octahydro-1H-benzo3,4]cyclohepta[1,2-c]pyridine;

and salts thereof.

The pharmaceutical compositions of this invention are preferably in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of psychiatric disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I above, including the novel compounds according to the invention, may be prepared by a process which comprises reacting a compound of formula $R^1$-L with a compound of formula III:

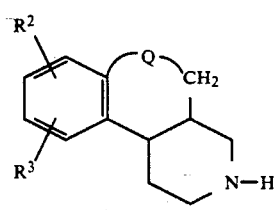
(III)

wherein Q, $R^1$, $R^2$ and $R^3$ are as defined above; and L represents a leaving group.

The leaving group L is suitably halogen, for example bromine.

The reaction is conveniently carried out in the presence of a mild base such as potassium carbonate, in a suitable solvent, e.g. N,N-dimethylformamide, suitably at an elevated temperature, for example a temperature in the region of 100° C.

The intermediates of formula III above may be prepared by a process which comprises reducing a compound of formula IV:

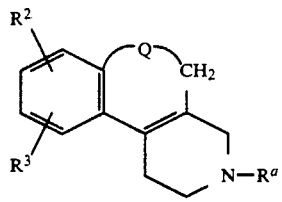
(IV)

wherein Q, $R^2$ and $R^3$ are as defined above, and $R^a$ represents an amino-protecting group; and subsequently removing the amino-protecting group $R^a$.

Suitable examples of amino-protecting groups for the substituent $R^a$ include carboxylic acid groups such as acetyl, chloroacetyl, trifluoroacetyl, formyl, benzoyl, phthaloyl, phenylacetyl or pyridinecarbonyl; acid groups derived from carbonic acid such as ethoxycarbonyl, benzyloxycarbonyl, t-butoxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl or t-amyloxycarbonyl; acid groups derived from sulphonic acid, e.g. p-toluenesulphonic acid; and other groups such as methyl, benzyl, trityl, o-nitrophenylsulphenyl or benzylidene.

Preferred amino-protecting groups are methyl, benzyl, benzyloxycarbonyl and t-butoxycarbonyl.

The removal of the amino-protecting group present in the resultant compound may be effected by an appropriate procedure depending upon the nature of the protecting group. For example, if $R^a$ represents methyl this group may be removed by treatment with cyanogen bromide at an elevated temperature, followed by work-up in a mineral acid such as aqueous hydrochloric acid, also at an elevated temperature.

In an alternative process, the compounds of formula I above, including the novel compounds according to the invention, may, where appropriate, be prepared directly by reduction of a compound of formula V:

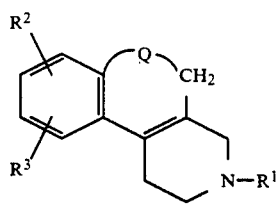

wherein $R^1$, $R^2$ and $R^3$ are as defined above.

The nature of the conditions employed for effecting the reduction of the compounds of formulae IV and/or V will largely be dependent on the stereochemistry of the ring junction between the piperidino moiety and the rest of the molecule desired in the final product. For example, if the cis isomer is desired, an appropriate method for reducing the precursor of formula IV or V may be catalytic hydrogenation. A suitable catalyst is platinum(IV) oxide, and the reaction is conveniently carried out in ethanol as solvent.

Alternatively, if the trans ring junction is desired, a suitable reducing agent may be lithium in liquid ammonia. The reaction is conveniently carried out in an inert organic solvent such as tetrahydrofuran, preferably in the presence of aniline, and suitably at a temperature in the region of $-78°$ C.

The intermediates of formulae IV and V above may, as appropriate, be prepared analogously to the method described in Can. J. Chem., 1974, 52, 2316 for the corresponding hexahydrobenz[f]isoquinolines. The synthetic route may be illustrated as follows:

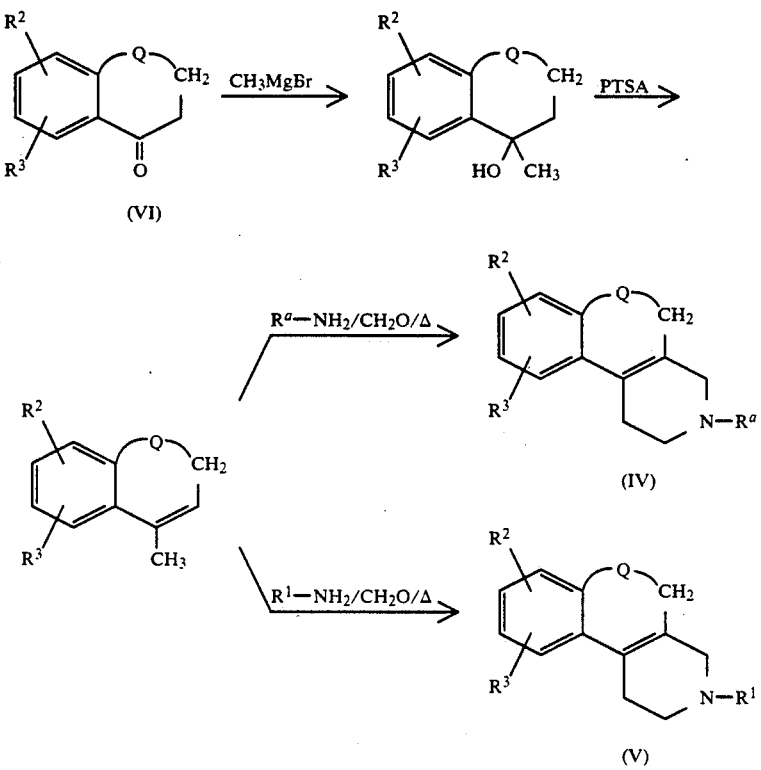

in which Q, $R^1$, $R^2$, $R^3$ and $R^a$ are as defined above; and PTSA is an abbreviation for p-toluenesulphonic acid.

The compounds of formula VI above, where they are not commercially available, can be prepared by the methods described in J. Org. Chem., 1962, 27, 70, or by methods analogous thereto.

Except where explicitly stated otherwise, the above-described processes are likely to give rise to mixtures of stereoisomers. At an appropriate stage, these isomers may be separated by conventional techniques such as preparative chromatography.

The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene, *Protective Groups in Organic Synthesis*, John Wiley & Sons, 1981. The protecting groups may be removed at a convenient subsequent stage using methods known from the art.

Displacement of Tritiated Sigma Ligand

In vitro activity

Binding of test compounds to the sigma site in vitro was determined by the method of Weber et al., *Proc. Natl. Acad. Sci. USA*. 1986, 83, 8784. The compounds of the accompanying Examples displaced tritiated di-tolyl guanidine (DTG) from sigma sites with potencies better than 200 nM.

EXAMPLE 1

2-Butyl-2,3,4,4a,9,9a-hexahydro-1H-indeno[2,1-c]pyridine

Step 1: 1-Hydroxy-1-methyl-2,3-dihydro-1H-indene

A solution of 25.05 g (0.190 mol) of 1-indanone in 250 ml of anhydrous ether was added over 45 min to a solution of 81.0 ml (0.243 mol) of 3.0M methyl magnesium bromide in ether under $N_2$ whilst stirring magnetically. After completion of the addition, the reaction was heated to reflux for 40 min, allowed to cool, then quenched with 30 ml of saturated ammonium chloride solution. The ether layer was decanted from a white solid, washed with water ($2 \times 100$ ml), then with saturated sodium chloride solution (100 ml), dried ($K_2CO_3$) and evaporated in vacuo to leave 24.64 g (88%) of the title product as an orange oil. NMR $\delta(CDCl_3)$ 1.57 (3H, s), 2.16-2.24 (2H, m), 2.77-2.89 (1H, m), 2.97-3.09 (1H, m) 7.23-7.38 (4H, m).

Step 2: 3-Methyl-1H-indene

A solution of 24.64 (0.166 mol) of 1-hydroxy-1-methyl-2,3-dihydro-1H-indene and 0.30 g of p-toluenesulphonic acid monohydrate in 300 ml of toluene was heated to reflux for 3 h with water being collected by means of a Dean Stark trap. The reaction mixture was cooled, washed with water ($3 \times 100$ ml), then with saturated sodium chloride solution (100 ml), dried ($K_2CO_3$) and evaporated in vacuo to leave an orange oil. This was vacuum distilled to yield 14.57 g (67%) of the title product as a colourless oil, b.p. 32°-35° C./0.3 mm of Hg. NMR $\delta(CDCl_3)$ 2.17 (3H, m), 3.31 (2H, m), 6.20 (1H, m), 7.16-7.35 (3H, m), 7.45 (1H, m).

Step 3:
2-Butyl-2,3,4,9-tetrahydro-1H-indeno[2,1-c]pyridine

A solution of 3.01 g (23.1 mmol) of 3-methyl-1H-indene and 7.51 ml of a 37% solution of formaldehyde (92.5 mmol) in 25 ml of acetic acid was heated at 70° C. for 30 min with stirring. While maintaining the temperature below 70° C., 5.83 g (53.2 mmol) of n-butylamine hydrochloride was added and the mixture was stirred at 70° C. for 3 h under nitrogen. The solution was cooled to room temperature, diluted with water (100 ml) and washed with ether ($3 \times 100$ ml). The aqueous layer was made toxic with 50% sodium hydroxide solution and extracted with ether ($3 \times 100$ ml). The combined ether extracts were dried ($K_2CO_3$) and evaporated in vacuo to leave 6.64 g of green oil. Some (2.60 g) was chromatographed on flash silica, eluting with 5-7% methanol/dichloromethane, then on alumina, eluting with 2-7% ethyl acetate/petroleum ether to give 0.098 g (5%) of the title product as a yellow oil. The hydrochloride salt was made using ethereal hydrogen chloride. Upon evaporation of the solvent and recrystallisation from ethanol/ethyl acetate the title product hydrochloride was obtained as a pale yellow solid, m.p. 196°-200° C. (dec). NMR $\delta(D_2O/DCl)$ 0.96 (3H, t, J=7.3 Hz), 1.43 (2H, m), 1.81 (2H, m), 2.92 (2H, m), 3.31-3.46 (5H, m), 3.79 (1H, m), 4.08 (1H, m), 4.36 (1H, m), 7.30-7.33 (1H, m), 7.40 (2H, m), 7.55-7.57 (1H, m), m/z (CI+, $NH_3$) 228 (M+H)+, 184 (M-$CH_2CH_2CH_3$)+ Analysis calcd. for $C_{16}H_{22}Cl$ N: C, 72.85; H, 8.41; N, 5.31%. Found: C, 72.61; H, 8.38; N, 5.25%.

Step 4:
2-Butyl-2,3,4,4a,9,9a-hexahydro-1H-indeno[2,1-c]pyridine

A solution of 2.02 g of crude 2-butyl-2,3,4,9-tetrahydro-1H-indeno[2,1-c]pyridine in 40 ml of anhydrous THF and 1.0 ml of aniline was added to a solution of 0.456 g of lithium wire in 250 ml of liquid ammonia, cooled by a dry-ice/acetone bath. The mixture was stirred at −78° C. for 1½ h under nitrogen before quenching carefully with water and allowing the solvents to evaporate overnight. The residue was partitioned between ether and water and the aqueous layer was re-extracted with more ether. The combined ether extracts were dried ($K_2CO_3$) and evaporated in vacuo to leave 2.69 g of brown oil. This was purified by chromatography on flash silica, eluting with 5-7% methanol/dichloromethane, then on alumina, eluting with 2-5% ethyl acetate/petroleum ether to yield 0.079 g of the title product as a colourless oil. The hydrochloride salt was made using ethereal hydrogen chloride. Upon evaporation of the solvent and recrystallisation from ethanol/ethyl acetate the title product hydrochloride was obtained as a white solid, m.p. 159°-163° C. NMR $\delta$ at 358K ($D_2O$) 0.91 (3H, t, J=7.3 Hz), 1.37 (2H, m), 1.67 (2H, m), 2.36 (2H, m), 2.65 (2H, m), 2.85-3.05 (4H, m), 3.13 (1H, d of d, J=15.9 and 6.2 Hz), 3.33-3.46 (3H, m), 7.28-7.38 (4H, m). m/z (CI+, $NH_3$) 230 (M+H)+, 186 (M-$CH_2CH_2CH_3$)+.

EXAMPLE 2

3-Butyl-2,3,4,4a,5,6,7,11b-octahydro-1H-benzo[3,4]cyclohepta[1,2-c]pyridine

Step 1:
5-Hydroxy-5-methyl-6,7,8,9-tetrahydro-5H-benzocycloheptene

Following the procedure of Example 1, step 1, 26.02 g (0.162 mol) of 1-benzosuberone in 250 ml of anhydrous ether was reacted with 68.0 ml (0.204 mol) of 3.0M methyl magnesium bromide in ether to afford 26.65 g (93%) of the title product as a yellow oil. NMR $\delta(CDCl_3)$ 1.59 (3H, s), 1.77-1.97 (6H, m), 2.83-2.96 (2H, m), 7.06-7.24 (3H, m), 7.67 (1H, d of d, J=7.6 and 1.5 Hz).

Step 2: 9-Methyl-6,7-dihydro-5H-benzocycloheptene

Following the procedure of Example 1, step 2, 26.65 g (0.151 mol) of 5-hydroxy-5-methyl-6,7,8,9-tetrahydro-5H-benzocycloheptene in 300 ml of toluene was reacted with 0.30 g of p-toluenesulphonic acid monohydrate. Vacuum distillation yielded 19.17 g (80%) of the title product as a colourless oil, b.p. 62°-65° C./1.0 mm of Hg. NMR $\delta(CDCl_3)$ 1.81 (2H, q, J=7.1 Hz), 2.07 (2H, m), 2.09 (3H, s), 2.56 (2H, t, J=6.9 Hz), 6.97 (1H, m), 7.14-7.26 (4H, m).

Step 3:
3-Butyl-2,3,4,4a,5,6,7,11b-octahydro-1H-benzo[3,4]cyclohepta[1,2-c]pyridine Following the procedure of Example 1, step 3, 1.02 g (6.46 mmol) of 9-methyl-6,7-dihydro-5H-benzocycloheptane in 7 ml of acetic acid was reacted with 2.10 ml of 37% formaldehyde solution and 1.63 g of butylamine hydrochloride. Work up afforded 1.55 g of crude 3-butyl-2,3,4,5,6,7-hexahydro-1H-benzo[3,4]cyclohepta[1,2-c]pyridine as a pale yellow oil.

Following the procedure of Example 1, step 4, this was reacted with 0.52 g of lithium wire in 250 ml of liquid ammonia, 40 ml of anhydrous THF and 1 ml of aniline. Chromatography on flash silica, eluting with 5-7% methanol/dichloromethane, then on alumina, eluting with 2-3% ethyl acetate/petroleum ether gave 0.349 g (21%) of the title product as a colourless oil. The hydrochloride salt was made using ethereal hydrogen chloride. Upon evaporation of the solvent and recrystallisation from ethyl acetate/ethanol, the title product hydrochloride was obtained as a white solid, m.p. 185°-190° C. (dec). NMR δ(D$_2$O) 0.95 (3H, t, J=7.4 Hz), 1.36-1.47 (4H, m), 1.71-1.80 (4H, m), 1.92-1.99 (1H, m), 2.26-2.32 (2H, m), 2.81-3.19 (7H, m), 3.49 (1H, m), 3.77 (1H, m), 7.24-7.33 (4H, m). m/z (CI+, NH$_3$) 258 (M+H)$^+$, 214 (M-CH$_2$CH$_2$CH$_3$)$^+$. Analysis calcd. for C$_{18}$H$_{28}$ClN: C, 73.57; H, 9.60; N, 4.77%. Found: C, 73.54; H, 9.55; N, 4.74%.

EXAMPLE 3

3-Cyclohexyl-2,3,4,4a,5,6,7,11b-octahydro-1H-benzo[3,4]-cyclohepta[1,2-c]pyridine Following the procedure of Example 1, step 3, 2.0 g (12.6 mmol) of 9-methyl-6,7-dihydro-5H-benzocycloheptane in 14 ml of acetic acid was reacted with 4.2 ml of 37% formaldehyde solution and 3.95 g of cyclohexylamine hydrochloride. Work up yielded 9.25 g of crude 3-cyclohexyl-2,3,4,5,6,7-hexahydro-1H-benzo[3,4]cyclohepta[1,2-c]pyridine as a pale pink oil.

Following the procedure of Example 1, step 4, this was reacted with 1 g of lithium wire in 500 ml of liquid ammonia, 80 ml of anhydrous THF and 2 ml of aniline. Chromatography on flash silica, eluting with 5% methanol/dichlormethane, then on alumina, eluting with 3% ethyl acetate/petroleum ether gave 0.413 g (12%) of the title product as a colourless oil. The hydrochloride salt was made using ethereal hydrogen chloride. Upon evaporation of the solvent and recrystallisation from ethyl acetate/ethanol, the title product hydrochloride was obtained as a white solid, m.p. 272°-275° C. NMR δ(D$_2$O) 1.13-1.24 (1H, m), 1.31-1.57 (6H, m), 1.68-1.79 (3H, m), 1.91-1.95 (3H, m) 2.10-2.12 (2H, m), 2.24-2.36 (2H, m), 2.80-2.86 (1H, m), 2.92-3.05 (3H, m), 3.14-3.26 (2H, m), 3.40 (1, m), 3.68 (1H, m), 7.24-7.33 (4, m). m/z (CI+, NH$_3$) 2.84 (M+H)$^+$, 240.

EXAMPLE 4

Tablet Preparation

Tablets containing 1,0, 2.0, 25.0, 26.0, 50.0 and 100.0 mg, respectively of the following compounds are prepared as illustrated below:
2-Butyl-2,3,4,4a,9,9a-hexahydro-1H-indeno[2,1-c]pyridine
3-Butyl-2,3,4,4a,5,6,7,11b-octahydro-1H-benzo[3,4]cyclohepta[1,2-c]pyridine
3-Cyclohexyl-2,3,4,4a,5,6,7,11b-octahydro-1H-benzo[3,4]cyclohepta[1,2-c]pyridine

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 28.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

What is claimed is:

1. A compound of formula IIA or a salt thereof:

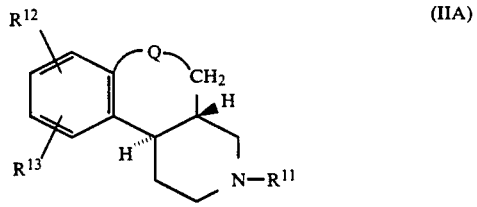

(IIA)

wherein

Q represents a bond or a group of formula —(CH$_2$)$_2$—;

R$^{11}$ is selected from the group consisting of C$_{3-6}$ alkyl, C$_{2-6}$ alkenyl, C$_{3-10}$ cycloalkyl, C$_{3-7}$ cycloalkyl (C$_{1-6}$) alkyl and aryl (C$_{1-6}$) alkyl; and R$^{12}$ and R$^{13}$ both represent hydrogen.

2. A compound of formula IIB or a salt thereof:

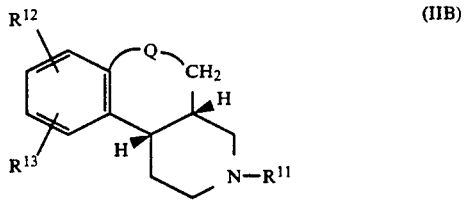

(IIB)

wherein

Q represents a bond or a group of formula —(CH$_2$)$_2$—;

R$^{11}$ is selected from the group consisting of C$_{3-6}$ alkyl, C$_{2-6}$ alkenyl, C$_{3-10}$ cycloalkyl, C$_{3-7}$ cycloalkyl (C$_{1-6}$)alkyl and aryl(C$_{1-6}$) alkyl; and R$^{12}$ and R$^{13}$ both represent hydrogen.

3. A compound selected from: 2-butyl-2,3,4,4a,9,9a-hexahydro-1H-indeno[2,1-c]pyridine; 3-butyl- 2,3,4,4a,5,6,7,11b-octahydro-1H-benzo[3,4]-cyclohepta[1,2-c]pyridine; 3-cyclohexyl-2,3,4,4a,5,6,7,11b-octahydro-1H-benzo-[3,4]cyclohepta[1,2-c]pyridine; and pharmaceutically acceptable salts thereof.

4. A pharmaceutical composition comprising an effective amount of a compound of formula IIA as defined in claim 1 or a pharmaceutically acceptable salt thereof in association with one or more pharmaceutically acceptable carriers and/or excipients.

5. A pharmaceutical composition comprising an effective amount of a compound of formula IIB as defined in claim 2 or a pharmaceutically acceptable salt thereof in association with one or more pharmaceutically acceptable carriers and/or excipients.

6. A pharmaceutical composition comprising an effective amount of a compound according to claim 3 or a pharmaceutically acceptable salt thereof in association with one or more pharmaceutically acceptable carriers and/or excipients.

* * * * *